United States Patent [19]

Greff et al.

[11] 4,242,310

[45] Dec. 30, 1980

[54] STERILE CONNECTION APPARATUS

[75] Inventors: Richard Greff, Ingleside; Ludwig Wolf, Jr., Crystal Lake; John Munsch, Libertyville; Layton C. Kinney, Chicago, all of Ill.

[73] Assignee: Baxter Travenol Laboratories, Inc., Deerfield, Ill.

[21] Appl. No.: 959,610

[22] Filed: Nov. 13, 1978

[51] Int. Cl.$^3$ .............................................. A61L 2/00
[52] U.S. Cl. .......................................... 422/300; 312/1
[58] Field of Search ................... 128/1 R, 1 B; 312/1, 312/209, 3, 31, 31.2; 422/292, 300, 26, 305; 285/18

[56] References Cited

U.S. PATENT DOCUMENTS

| | | | |
|---|---|---|---|
| 1,948,239 | 2/1934 | Redd | 422/300 |
| 2,219,564 | 10/1940 | Reyniers | 312/1 |
| 2,901,143 | 8/1959 | Pope | 312/1 |
| 3,410,619 | 11/1968 | Delnay et al. | 312/1 |
| 3,536,370 | 10/1970 | Evans et al. | 128/1 R |
| 3,719,017 | 3/1973 | Shapiro et al. | 422/28 |

OTHER PUBLICATIONS

"Controlled Environment Animal Care Laboratory Germfree Equipment", by Germfree Laboratories Inc., 1965.

Primary Examiner—S. Leon Bashore
Assistant Examiner—Michael Goldman
Attorney, Agent, or Firm—Paul C. Flattery; George H. Gerstman

[57] ABSTRACT

A sterile connection apparatus is provided for enabling the connection of a first tube to a transfer tube of a medical solution container. The apparatus includes a housing having a cover portion which is adapted for interfitting with a base portion to provide a substantially closed interior volume. The first tube and the transfer tube of the medical solution container are introduced within the interior volume and the housing carries means located therewithin and operable from the outside of the housing for enabling manipulation of one of the tubes. In this manner, the first tube may be disconnected from and/or connected to the transfer tube. Means are provided for sterilizing the tubes within the substantially closed interior volume.

2 Claims, 3 Drawing Figures

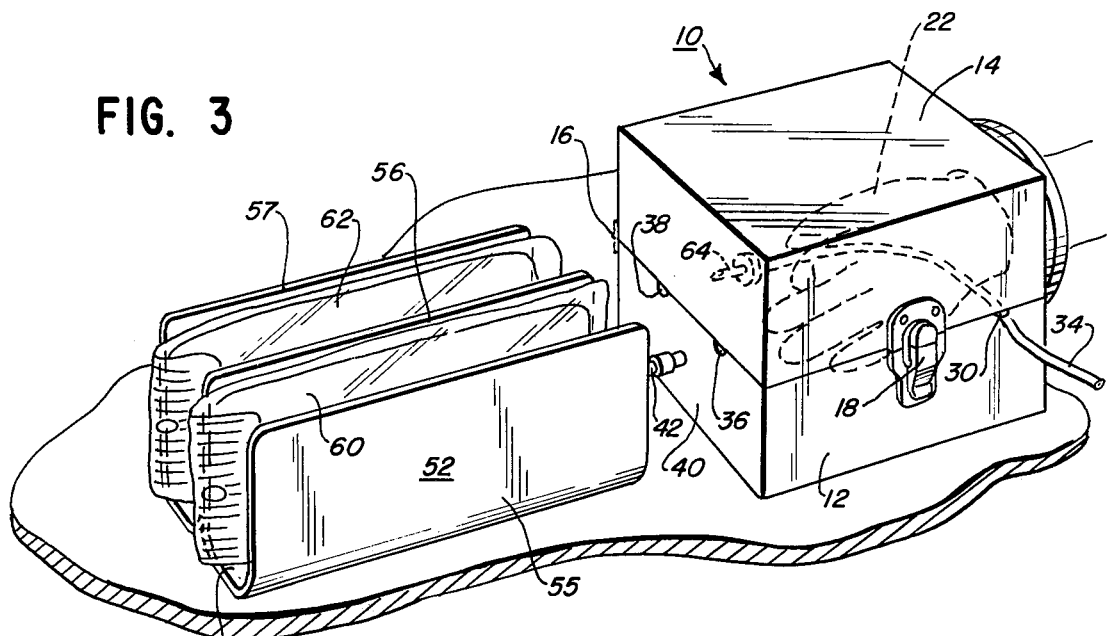
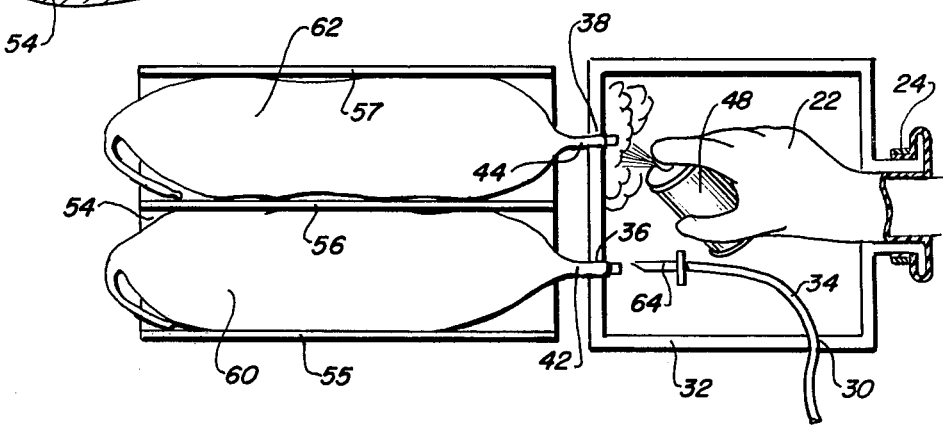
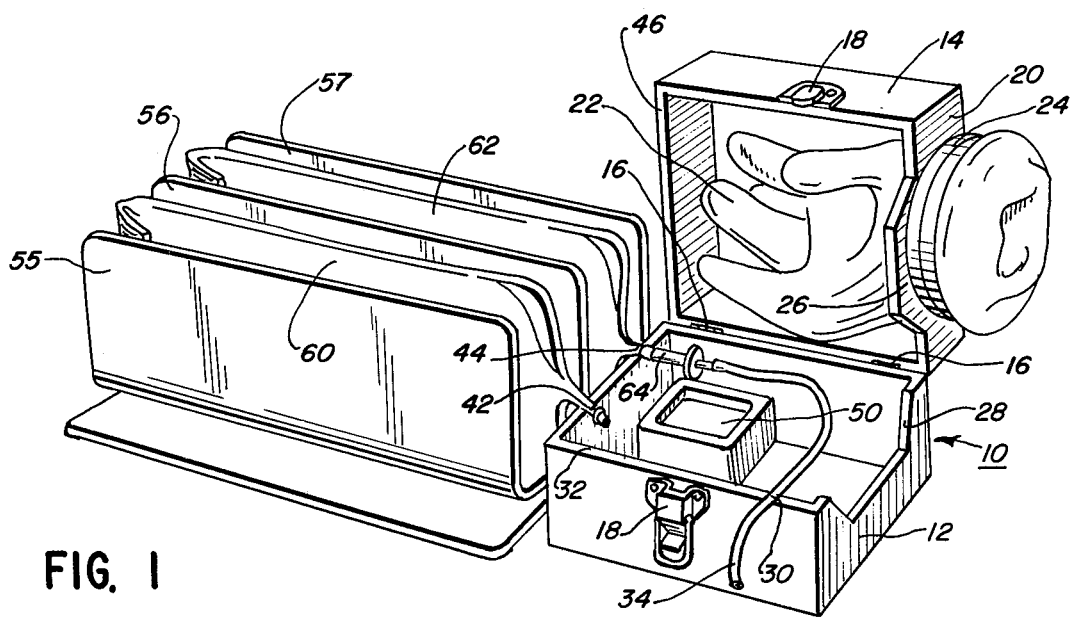

STERILE CONNECTION APPARATUS

BACKGROUND OF THE INVENTION

The present invention concerns an apparatus for enabling the sterile connection of a first tube to a transfer tube of a medical solution container. Although the illustrative embodiment of the invention is described in connection with tube transfer during ambulatory peritoneal dialysis, it is to be understood that other sterile tube transfers can be achieved in accordance with the present invention, such as the transfer of a tube from one blood bag to another. Thus, as used herein, the term "medical solution container" is intended to encompass containers of all shapes and materials and including any type of solution which may be introduced to a patient for medical purposes.

In many medical applications, it is necessary to remove a connector tube from a first medical solution container and to then introduce it to a second medical solution container. It is, of course, desirable and, on occasion, required that the transfer of the tube from one medical solution container to the other medical solution container be achieved in a sterile manner.

For example, in one type of ambulatory peritoneal dialysis, a tube which is coupled to the patient's peritoneal cavity is first connected to the transfer port (i.e., transfer tube) of a fresh dialysate solution container. For ambulatory purposes, the container is preferably in the form of a flexible plastic bag.

The dialysate solution is then introduced into the patient's peritoneal cavity via the transfer tube and the patient's tube and the dialysate solution is allowed to remain in the patient's peritoneal cavity for several hours, for example three to four hours. During this period of time, the patient's tube is not disconnected from the transfer tube, but the patient's tube may be clamped and the dialysate solution bag may be folded and carried by the patient.

Thereafter, the patient's tube is unclamped and the dialysate solution is drained back into the solution bag. Once the dialysate solution has been drained into the solution bag, the patient's tube is disconnected from the transfer tube of the used solution container and is inserted into the transfer tube of a fresh solution container. Thereupon the procedure is repeated. It is desirable, however, that during the disconnection of the patient's tube from the used dialysate solution container and connection of the patient's tube to a fresh dialysate solution container, that such connection be accomplished in a sterile manner. In addition, other medical procedures utilize similar connections which may desirably be accomplished in a sterile manner.

For example, in blood administration a tube coupled to a patient's vein is first inserted into the transfer port of a fresh blood bag. After the blood has been introduced from the fresh blood bag to the patient, it may be necessary to introduce blood from another blood bag to the patient. Under such conditions, the patient's tube is removed from the transfer port of the first blood bag and is inserted into the transfer port of another blood bag. The desirability of accomplishing such transfer in a sterile manner is apparent.

It is, therefore, an object of the present invention to provide a system for enabling the sterile transfer of a first tube from the transfer tube of a first medical container and to the transfer tube of another medical container.

Another object of the present invention is to provide sterile connection apparatus that is simple in construction and easy to manufacture.

A further object of the present invention is to provide a method for enabling a patient to connect, in a sterile manner, (a) a tube coupled to the patient to (b) a transfer tube of a medical solution container.

Other objects and advantages of the present invention will become apparent as the description proceeds.

SUMMARY OF THE INVENTION

In accordance with the invention, sterile connection apparatus is provided for enabling the connection of a first tube to a transfer tube of a medical solution container. The apparatus comprises a housing including a base portion and a cover portion. The portions are adapted for interfitting with each other to provide a substantially closed interior volume.

The housing includes means for receiving the first tube and means for receiving the transfer tube from a medical solution container. The housing carries means which are located within the housing and operable from outside the housing for enabling manipulation of one of the tubes with respect to the other tube. Means are provided for sterilizing the tubes within the substantially closed interior volume.

In the illustrative embodiment, the housing includes hinge means connecting the base portion to the cover portion. Locking means are provided for maintaining the base portion and the cover portion in their closed position during manipulation of the tube.

In the illustrative embodiment, the receiving means comprises grooves defined by one of the base portion and cover portion. The manipulation means comprises a glove extending into the interior of the housing and the sterilization means comprises a container of sterilizing solution located within the housing and adapted for manipulation by the glove.

In the illustrative embodiment, the housing is substantially light-transmissive to enable viewing of the interior volume from the exterior thereof when the base portion and cover portion are in their closed position. A rack is provided for holding a pair of medical solution containers adjacent each other for enabling easy insertion of the transfer tubes into the housing's receiving means. The rack comprises a base having three generally parallel members extending therefrom whereby a medical solution container may be positioned between two of the three members.

A more detailed explanation of the invention is provided in the following description and claims, and is illustrated in the accompanying drawings.

BRIEF DESCRIPTION OF THE DRAWINGS

FIG. 1 is a perspective view of sterile connection apparatus constructed in accordance with the principles of the present invention;

FIG. 2 is a top view thereof, with a portion thereof shown in cross-section for clarity and with the cover portion of the housing removed for clarity; and FIG. 3 is a perspective view, in partially exploded form, of the sterile connection apparatus of FIG. 1.

DETAILED DESCRIPTION OF THE ILLUSTRATIVE EMBODIMENT

Referring to the drawings, a housing 10 which is preferably rectilinear in form, includes a lower base portion 12 and a cover 14 connected thereto by means of a pair of hinges 16. Cover 14 is pivotable from an open position (FIG. 1) about the axes of hinges 16 to a closed position (FIG. 3). A locking device 18 is provided to maintain the housing in its closed position as desired. The housing is preferably formed of a transparent plastic material so as to enable viewing of the interior thereof from the exterior thereof while the cover 14 is in its closed position.

One vertical side 20 of cover 14 defines an opening for receiving a glove 22 which extends into the cover in a generally horizontal direction. A band 24 is fastened to side 20 and to glove 22 for maintaining glove 22 in place with respect to cover 14. Glove 22 is preferably formed of extremely flexible rubber or plastic material, as is well-known in the medical glove art, and the opening defined by side 20 is such that a seal is provided when the cover 14 is closed. Side 20 of cover 14 has an extended portion 26 which interfits with recessed portion 28 of base 12. Extended portion 26 enables the positioning of ring 24 on the cover 14 without requiring a larger size housing.

A first groove 30 is defined by the top edge 32 of base 12, for receiving tube 34 from a patient. In ambulatory peritoneal dialysis applications, tube 34 could be connected to a catheter which is coupled to the patient's peritoneal cavity. In blood administration, tube 34 could be connected to a fitting which is coupled to the vein of the patient.

Two other grooves 36 and 38 are also defined along top edge 32 of base 12, on side 40 of base 12. Grooves 36 and 38 are adapted for receiving the transfer ports 42 and 44 of medical solution containers. It has been found that by providing grooves 30, 36 and 38 along top edge 32 of base 12, and by utilizing a generally planar bottom edge 46 of cover 14, when the tubes 34, 42 and 44 are inserted into the grooves and the cover 14 is closed, the tubes will be held in place yet not clamped closed so long as the grooves 30, 36 and 38 are sufficiently dimensioned. Of course, if desired, the grooves 30, 36 and 38 could be defined by bottom edge 46 of cover 14 and top edge 32 of base 12 could be generally planar. Further, using appropriate dimensions both top edge 32 and bottom edge 46 could be grooved for receiving the tubes 30, 42 and 44.

A sterilization device is located within housing 10. As illustrated in FIG. 2, a spray can of a sterilizing agent, such as Betadine or hydrogen peroxide is provided. In the embodiment of FIG. 1, a steam generator 50 is located within housing 10 for generating steam to sterilize the items within the housing. Other sterilizing agents may be used, such as ozone, ethylene oxide or ultraviolet light. Further, a sterilizing solution could be placed within the housing and the solution could be applied by cloth or cotton to the parts within the housing.

A rack 52 is provided for holding the medical solution containers in place during sterilization. Rack 52 comprises a horizontal base 54 with three members 55, 56 and 57 extending vertically upwardly therefrom. A first medical solution container 60 is placed between members 55 and 56 and a second medical solution container 62 is placed between members 56 and 57, as illustrated in the drawings. Medical solution containers 60 and 62 are preferably of the flexible bag type. The operation of the system will now be described with respect to ambulatory peritoneal dialysis. Assume that the patient has drained the solution from his peritoneal cavity back into solution bag 62. Solution bag 62 is placed between members 56 and 57 and transfer port 44 is inserted into groove 38 while cover 14 is open. Tube 34, which is coupled to the patient's peritoneal cavity, is inserted into groove 30. A fresh dialysate solution bag 60 is placed between members 55 and 56 and its transfer port 42 is placed into groove 36.

Once tubes 34, 44 and 42 have been placed into grooves 30, 38 and 36, respectively, cover 14 is closed and locked by means of lock 18. Thereafter, the sterilizing agent may be utilized. For example, the steam generator 50 may be activated so that the contents of the housing are sterilized. The patient can then insert his hand into glove 22, remove spike 64 (which is connected to the end of tube 34) from transfer port 44 and insert spike 64 into transfer port 42 of fresh dialysate solution container 60. As illustrated in the FIG. 2 embodiment, the patient may spray a sterilization agent on the transfer ports while the cover 14 is closed, to sterilize the transfer ports. It may be desirable to utilize the sterilization agent while spike 64 is connected to transfer port 44, also while spike 64 is removed from both transfer ports and also after spike 64 has been inserted into transfer port 44. On the other hand, it may be found desirable to utilize the sterilization agent only during one or two of these transfer positions of spike 64.

Instead of utilizing a glove which extends into the housing, it may be desirable to utilize a mechanical linkage which can be operated from the outside of the housing. Such remotely controlled mechanical linkages are well-known in the art of handling radioactive materials, for example.

The patient may wish to use the sterile connection apparatus of the present invention for removing the patient's tube from a medical solution container and then capping the patient's tube instead of transferring it to another medical solution container. In this manner, only the patient's tube and the transfer port of the medical solution container to which the patient's tube is connected will be introduced into the housing. It can be seen that although certain illustrative embodiments of the invention have been shown and described, various modifications and substitutions may be made without departing from the novel spirit and scope of the present invention.

What is claimed is:

1. Sterile connection apparatus for enabling the connection of a first tube to a second tube, which comprises:

a housing including a base portion having a top edge and a cover portion having a bottom edge, said portions being adapted for interfitting with each other along their edges to provide a substantially closed interior volume;

said housing including means for receiving and holding said first tube and means for receiving and holding said second tube;

said receiving means comprising grooves in the edge of the base portion or the cover portion for receiving and holding said tubes with the portions of the tubes to be sterilized extending inside the housing and other portions of the tubes being outside the housing;

means carried by said housing, located within said housing and operable from outside said housing for enabling manipulation of one of said tube portions inside the housing with respect to the other tube portion inside the housing; and means for sterilizing said inside tube portions within the substantially closed interior volume.

2. Sterile connection apparatus as described in claim 1, wherein said housing includes hinge means connecting said base portion to said cover portion, and locking means for maintaining said base portion and cover portion in their closed position during manipulation of said tube.

* * * * *